(12) United States Patent
Ideker et al.

(10) Patent No.: US 9,757,577 B2
(45) Date of Patent: Sep. 12, 2017

(54) METHOD AND APPARATUS FOR HOSPITAL, EMT/EMS, AND AED GRADE EXTERNAL DEFIBRILLATION AND TRANSCUTANEOUS PACING

(71) Applicant: RUSE TECHNOLOGIES, LLC, Brookhaven, GA (US)

(72) Inventors: Raymond E. Ideker, Birmingham, AL (US); Richard B. Ruse, Brookhaven, GA (US); Scott Bohanan, Statesboro, GA (US)

(73) Assignee: Ruse Technologies, LLC, Brookhaven, GA (US)

( * ) Notice: Subject to any disclaimer, the term of this patent is extended or adjusted under 35 U.S.C. 154(b) by 0 days.

(21) Appl. No.: 14/881,975

(22) Filed: Oct. 13, 2015

(65) Prior Publication Data

US 2016/0101292 A1    Apr. 14, 2016

Related U.S. Application Data

(60) Provisional application No. 62/062,331, filed on Oct. 10, 2014.

(51) Int. Cl.
| | | |
|---|---|---|
| *A61N 1/39* | (2006.01) | |
| *A61N 1/362* | (2006.01) | |
| *A61N 1/04* | (2006.01) | |

(52) U.S. Cl.
CPC ......... *A61N 1/3906* (2013.01); *A61N 1/3625* (2013.01); *A61N 1/39* (2013.01); *A61N 1/046* (2013.01); *A61N 1/0492* (2013.01)

(58) Field of Classification Search
CPC .... A61N 1/3906; A61N 1/3625; A61N 1/046; A61N 1/0492
USPC ........................................................... 607/4
See application file for complete search history.

(56) References Cited

U.S. PATENT DOCUMENTS

| | | | |
|---|---|---|---|
| 5,206,602 A * | 4/1993 | Baumgartner | A61B 5/04004 330/258 |
| 7,920,918 B2 | 4/2011 | Ideker et al. | |
| 7,983,748 B2 | 7/2011 | Ruse | |
| 7,986,992 B2 * | 7/2011 | Ideker | A61N 1/3906 607/5 |
| 8,175,702 B2 | 5/2012 | Efimov et al. | |
| 8,509,889 B2 | 8/2013 | Efimov et al. | |

(Continued)

*Primary Examiner* — Christopher D Koharski
*Assistant Examiner* — Roland Dinga
(74) *Attorney, Agent, or Firm* — William H. Dippert; Laurence A. Greenberg; Werner H. Stemer

(57) ABSTRACT

A method and apparatus for treating a cardiac condition in a human or animal patient comprises contacting an area of skin spanning the chest area of the patient with at least two patches or electrode paddles that apply low voltages and currents in a rotational manner to pre-stimulate that area, followed by applying a high voltage shock in rapid succession through the patient's heart through at least two electrode pad patches or paddles, wherein an amplifier-based external defibrillation cardioversion system is used. Also, an external pacing system is employed using ascending ramp or any arbitrary ascending or level waveform for transcutaneous pacing which employ a constant current delivery mode. Treatable conditions include atrial fibrillation (AF), atrial tachycardia (AT), ventricular fibrillation (VF), and ventricular tachycardia (VT).

24 Claims, 5 Drawing Sheets

(56) References Cited

U.S. PATENT DOCUMENTS

| | | |
|---|---|---|
| 8,560,066 B2 | 10/2013 | Efimov et al. |
| 8,639,325 B2 | 1/2014 | Efimov et al. |
| 8,874,208 B2 | 10/2014 | Efimov et al. |
| 9,067,079 B2 | 6/2015 | Efimov et al. |
| 9,526,907 B2 | 12/2016 | Efimov et al. |
| 2004/0002736 A1 | 1/2004 | Waltman |
| 2004/0039419 A1 | 2/2004 | Stickney et al. |
| 2014/0005737 A1 | 1/2014 | Kozin et al. |
| 2014/0094869 A1 | 4/2014 | Walker et al. |

* cited by examiner

METHOD AND APPARATUS FOR HOSPITAL, EMT/EMS, AND AED GRADE EXTERNAL DEFIBRILLATION AND TRANSCUTANEOUS PACING

CROSS-REFERENCE TO RELATED APPLICATION

This patent is based upon and claims the benefit of the filing date of commonly assigned U.S. Provisional Patent Application Ser. No. 62/062,331, filed Oct. 10, 2014, which application is incorporated herein in its entirety.

FIELD OF THE INVENTION

This invention is directed to the electrical management of cardiac arrhythmias or abnormal heart rhythms that occur in the electrical systems of the atrial or ventricular chambers of the human heart. More particularly, the invention is directed to the treatment of ventricular fibrillation, ventricular tachycardia, atrial fibrillation, or atrial tachycardia, by external defibrillation and/or cardioversion.

BACKGROUND OF THE INVENTION

Ventricular fibrillation (VF) is a cause of cardiac arrest and sudden cardiac death. During VF, the ventricular muscle contracts in a much less organized pattern than during normal sinus rhythm, so the ventricles fail to pump blood into the arteries and systemic circulation. VF is a sudden, lethal arrhythmia responsible for many deaths in the Western world, mostly brought on by ischemic heart disease. VF, which occurs in approximately 2 out of 10,000 people per year, is a medical emergency. If the arrhythmia continues for more than a few seconds, blood circulation will cease as evidenced by lack of pulse, blood pressure and respiration, and death will occur.

Despite much work, the underlying nature of VF is not completely understood. Most episodes of VF occur in diseased hearts, but other episodes occur in structurally normal hearts. Much work still has to be done to understand the mechanisms of VF.

Ventricular tachycardia (VT) is a tachyarrhythmia originating from an ectopic ventricular region, characterized by a rate typically greater than 100 beats per minute and wide QRS complexes. VT may be monomorphic, i.e., originating from a single repeating pathway with identical QRS complexes, or polymorphic, i.e., following changing pathways, with varying QRS complexes. Non-sustained VT is defined as an episode of tachycardia of less than 30 seconds duration; longer runs are considered sustained VT.

No absolute ECG criteria exist for establishing the presence of VT. However, several factors suggest VT, including the following: rate greater than 100 beats per minute (usually 150-200), wide QRS complexes (>120 ms), presence of AV dissociation, and fusion beats, which are integrated into the VT complex.

VT may develop without hemodynamic deterioration. Nevertheless, it often causes severe hemodynamic compromise and may deteriorate rapidly into VF. Therefore, this tachyarrhythmia also must be addressed swiftly to avoid morbidity or mortality.

VT is defined as three or more beats of ventricular origin in succession at a rate greater than 100 beats per minute. There are no normal-looking QRS complexes. The rhythm is usually regular, but on occasion it may be modestly irregular. The arrhythmia may be either well-tolerated or associated with grave, life-threatening hemodynamic compromise. The hemodynamic consequences of VT depend largely on the presence or absence or myocardial dysfunction (such as might result from ischemia or infarction) and on the rate of VT. AV dissociation usually is present, which means that the sinus node is depolarizing the atria in a normal manner at a rate either equal to, or slower than, the ventricular rate. Thus, sinus P waves sometimes can be recognized between QRS complexes. They bear no fixed relation to the QRS complexes unless the atrial and ventricular rates happen to be equal. Conduction from atria to ventricles is usually prevented because the AV node or ventricular conduction system is refractory due to ventricular depolarizations caused by the VT. VT is uncommon in the absence of apparent heart disease.

Myocardial infarcts heal by forming scar tissue, which can lead to VT. This can occur days, months, or years after the infarction. VT can also result from anti-arrhythmic medications (an undesired effect) or from altered blood chemistries (such as low potassium or magnesium levels), pH (acid-base) changes, or insufficient oxygenation.

Fast atrial arrhythmias such as atrial fibrillation (AF) and atrial tachycardia (AT) are abnormal heart rhythms which afflict around three million people each year in the United States. The most prevalent electrical manifestation of the disease electrically is a preponderance of irregular AF wavelets of activation. These irregular AF wavelets are frequently generated in the pulmonary veins (PVs) and are conducted into the left atrium and then the right atrium, causing chaotic and rapid activation that interferes with the normal sino-atrial and atrio-ventricular (SA/AV) node cardiac electrical pathways and generates rapid, irregular ventricular contractions. These irregular AF wavelets can be in the form of AF or atrial flutters, typical and atypical, which may vary in terms of severity and rate. AF makes the ventricular response so irregular and fast that it interferes with normal blood flow through the heart chambers, can lead to severe structural heart disease, and can be life-threatening if not treated effectively. While the irregular rate of ventricular contraction during AF and AT may compromise cardiac output and cause fatigue, much of the increased mortality associated with AF is due to clot formation resulting from poor circulation in the atria that embolizes to cause stroke, renal infarcts, etc. Persistent AF over weeks or months is particularly dangerous.

A procedure to treat AF, or AT is DC cardioversion shock therapy to convert AF/flutter to sinus rhythm. This is an excellent conversion tool; however, unless the underlying cause of the AF is resolved, it most likely will recur. Implantable cardioverter defibrillators (ICDs) have been used for conversion of AF; however, since the patient is conscious when the shock is delivered, many individuals find the discomfort of the shock intolerable.

All of the conditions described above can be treated by defibrillation, including external defibrillation. External defibrillation tends to be painful to the patient, whether applied in an automatic external defibrillator (AED), emergency medical technician/emergency medical services (EMT/EMS), or hospital setting. There is a need for external defibrillation that is less painful to the patient.

Objects of the Invention

It is an object of the invention to provide a novel amplifier-based method and system for external defibrillation in an AED, EMT/EMS, or hospital setting.

It is also an object of the invention to provide a method and system where a preliminary step prepares the patient for external defibrillation.

It is a further object of the invention to provide a method and system whereby through the use of pre-stimulus skeletal muscle rotation and contraction, no further muscle contraction is anticipated during the second step of the delivery of high-voltage shocks.

It is a yet further object of the invention to provide a method and system where a where a preliminary step prepares the patient for external defibrillation and the defibrillation is an amplifier-based external defibrillation and or cardioversion system.

It is a yet further object of the invention where an amplifier-based external defibrillation and or cardioversion system can deliver arbitrary waveforms, including ascending ramp, ascending exponential, level, curved or any other waveform for phase 1 and phase 2 which are useful in the science of defibrillation and cardioversion.

It is a yet further object of the invention to provide a method and system where the high voltage shocks employ increasing energy with increasing time waveforms, reducing peak voltages and lowering chest impedance.

It is a yet further object of the invention to provide a method and system wherein arbitrary waveforms and a slower rate of change are employed, as well as reduced peak voltages, in defibrillation.

It is a yet further object of the invention to provide a method and system whereby perceived pain as well as the traditional first-, second- and sometimes third-degree burns on a patient's skin under external electrodes will be greatly reduced.

It is a yet further object of the invention to provide a method and system for cardioversion and defibrillation whereby if the first cardioversion or defibrillation shock fails, another shock comprised of different biphasic wave forms may be selected to enhance and capture outlier patients who are difficult to cardiovert or defibrillate, thereby increasing the overall rescue rate for patients that require cardioversion and or defibrillation.

It is a yet further object of the invention to provide a method and system whereby phase 1 and phase 2 arbitrary waveforms may be mixed and matched to ensure a higher rate of conversion.

It is a yet further object of the invention to provide a method and system for creating phase 2 waveforms whereby the shock voltage may be "hard-switched" negative with respect to the zero crossing point to any specified negative voltage potential.

It is a yet further object of the invention to provide a method and system using narrow phase 2 pulse widths between one and about three milliseconds to hyperpolarize the myocardium after the phase 1 shock has been delivered.

It is a yet further object of the invention to provide a method and system using narrow phase 2 pulse widths of any arbitrary geometry may be employed for phase 2 such as ascending ramp, ascending exponential, level, curved or any other waveform that hyperpolarize the myocardium after the phase 1 shock has been delivered.

These and other objects of the invention will become more apparent from the description and claims below.

SUMMARY OF THE INVENTION

This invention comprises a two-step amplifier based electrical pre-stimulus, external cardioversion/defibrillator delivery system and a capability to transcutaneously pace and/or deliver ascending and or arbitrary pacing waveforms stimulus to help restart an asystole heart in a hospital, EMT/EMS, or AED setting. External defibrillation is applied to a patient in essentially a two-step procedure. In a first step, a pre-stimulus servo amplifier array delivers low-voltage, electrical currents which are applied beneath defibrillator electrodes or patches to induce skeletal muscle rotation and contraction, to tighten muscle groups to a point where they can contract no further. This low-voltage electrical pre-stimulus prepares the muscle structures beneath the electrodes, stimulating them into an absolute refractory period (ARP) while lowering impedance in the chest and allowing for perceived pain reduction. In a second step, which is the actual cardioversion and defibrillation, high-voltage shocks are applied. Advantageously an amplifier-based external cardioverter/defibrillation system generates high voltage ascending waveform shocks comprising increasing energy with increasing time waveforms for therapies including AF, AT, VT and VF, such as arbitrary waveforms including ascending ramp, ascending exponential, rectilinear/level and ascending curved exponential waveforms. These waveforms increase efficiency, capture outlier patients who do not convert easily, reduce skin burning/damage, and reduce perceived pain. An integrated transcutaneous delivery system is onboard to stimulate and assist in restarting an asystole-heart using ascending or any arbitrary constant current waveforms that most efficiently pace the heart externally.

A cardiac defibrillation and or cardioversion waveform energy control system using differentially driven amplifier circuit topologies delivers biphasic arbitrary shock waveforms with increasing and or level energy with increasing time as represented by phase 1 ascending ramp, ascending exponential, ascending chopped, ascending stepped, ascending curved, square, rectilinear or level and or any combination of geometric shaped ascending or level waveforms which may be mixed or matched for phase 1 and phase 2 waveforms. These waveforms are delivered by any selection of one or more of three circuit topology modes, which are (1) constant current, (2) constant voltage, and (3) constant energy. The software-controlled defibrillation and or cardioversion shock waveforms control delivered defibrillation and/or cardioversion electrical shocks to convert cardiac arrhythmias and defibrillate the heart muscle.

A method and apparatus for an amplifier-based cardioversion/defibrillation includes using class A to Z or any other class of amplifier circuit topology to process arbitrary waveforms that deliver increasing energy with increasing time for a positive phase 1 and negative energy for Phase 2 time periods that can range from about 500 ns to about 100 ms pulsed, chopped or continuous waveforms using any voltage for phase 1 and phase 2 waveforms from about 0 V to about +/−2200 VDC.

In another embodiment, the cardiac defibrillation and/or cardioversion waveform energy control system uses the software-controlled defibrillation and/or cardioversion shock waveforms for the purpose of managing delivered shock energies by changing the curve and/or slope of ascending shocks using amplifier circuit topologies and software commands for the purpose of controlling delivered energy without changing peak voltage or changing the desired pulse width of a defibrillation or cardioversion shock.

In another embodiment of the invention, a method and an apparatus create phase 2 waveforms whereby the shock voltage is "hard-switched" negative with respect to the zero crossing point to any specified negative voltage potential, and preferably, using narrow phase 2 pulse widths between one to about three milliseconds to hyperpolarize the myocardium after the phase 1 shock has been delivered.

Pre-stimulation lowers the chest muscle mass impedance beneath the electrode patches. This should lower the overall high voltage shock energy used between patch electrodes. As it is performed now, defibrillation loses much of its voltage spreading through the chest before reaching the heart.

Using calculus mathematics as a reference, it is accepted that the "rate of change" during muscle contraction will be slowed remarkably via delivering low voltage ascending ramp pre-stimulation pulses that induce muscle rotation and contraction prior to a very high voltage shock. Only after the absolute refractory period is achieved is the high voltage shock delivered. During the high voltage shock, the muscles should not contract any further, thereby reducing or averting the violent and rapid muscle contractions that are now associated with the extreme pain of defibrillation or cardioversion. In addition, as the muscle mass surrounding and beneath the electrode patches or paddles have already been through their stimulation, ionization and contraction phases, the impedance in the chest beneath the electrodes is very low meaning the actual shock voltage targeted through the heart is more focused and will not spread as far across the surface of the chest. Electricity always takes the path of least resistance which, in this case, has already been "primed" for the shock pathway.

Most patients are more likely to cardiovert/defibrillate with a constant current shock because whatever the heart muscle impedance is adjusting to, this method delivers "constant current," which is specified by the software commands and delivered through the amplifiers. By definition the amplifiers can deliver a constant current into any load impedance by sampling the impedance characteristics of the signal which in this case is an ascending waveform. In the technology described herein, the ideal output waveform is constructed from discrete points in time or equations stored in the uC. At each discrete time point, on the order of microseconds, the uC outputs a new waveform value thru a Digital to Analog converter (DAC) to the amplifiers. At each discrete time point, the current through the load is digitally converted using an Analog to Digital converter (ADC). This digitized current is averaged over multiple time samples to create a rolling average. This rolling current average is used by the uC to calculate power and energy in real time for each discrete time point of the ideal output waveform. The uC then increases or decreases the ideal output waveform to maintain the desired constant current or to achieve the desired total energy at the completion of the waveform.

Constant current cardioverter/defibrillators that use ascending ramp type waveforms have not been known before. However, they would be most preferred as they will be more predictable in terms of rescue and consistent cardiac conversion.

In another aspect of the invention, a method for treating a cardiac condition in a human or animal patient, comprises:
contacting an area of skin of the patient with at least two patches or paddle electrodes that apply current in a rotational manner to pre-stimulate that area, and
applying a high voltage shock to the patient's heart through the at least two patches or paddle electrodes.

In another aspect of a method of the invention, an amplifier-based external defibrillation cardioversion system is used.

In another aspect of a method of the invention, the cardioversion system uses a two-step electrical stimulation comprising biphasic arbitrary and ascending ramp high-voltage shocks that employ increasing energy with increasing time waveforms which are used to reduce peak voltages, reduce cardioversion and defibrillation energy, capture those patients that don't easily cardiovert or defibrillate, reduce perception of pain and reduce or eliminate burning of skin beneath external electrodes.

In another aspect of a method of the invention, the system uses differentially driven amplifier circuit topologies whereby biphasic arbitrary shock waveforms deliver increasing and or level energy with increasing time as represented by phase 1 ascending ramp, ascending exponential, ascending chopped, ascending stepped, ascending curved, square, rectilinear or level and or any combination of geometric shaped ascending or level waveforms which are delivered by any selection of three modes of software controlled defibrillation and or cardioversion shock waveforms which are (1) constant current, (2) constant voltage, or (3) constant energy for the purpose of controlling delivered defibrillation and/or cardioversion electrical shocks to convert cardiac arrhythmias.

In another aspect of a method of the invention, arrhythmias are treated.

In another aspect of a method of the invention, qualified medical professionals first apply through mutual electrode delivery patches and use the system's electrical servo amplifier array stimulator to deliver pre-stimulus low voltage pulses to cause skeletal muscle rotation and contraction, comprising the absolute refractory period of muscle contraction and lowering chest impedance.

In another aspect of a method of the invention, in a second step a high voltage ascending waveform or any other biphasic arbitrary waveform shock is delivered, whether across the chest or between the front and back of a human chest, for conversion of AF, AT, VT or VF, delivering a high-voltage shock ascending or level waveform, which will reduce perceived pain by lowering peak voltages and chest impedance, and also greatly reduce or eliminating the traditional first, second- and sometimes third-degree burns on the patient's skin under external electrodes since arbitrary ramp waveforms and a slower rate of change for the delivered energy are achieved.

In another aspect of a method of the invention, if a first cardioversion or defibrillation shock fails, another shock comprised of different biphasic wave forms may be selected to enhance and capture outlier patients who are difficult to cardiovert or defibrillate thereby increasing the overall rescue rate for patients who require cardioversion and or defibrillation.

In another aspect of a method of the invention, the phase 2 shock voltage is "hard-switched" negative with respect to the zero crossing point to any specified negative voltage potential, and preferably, using narrow arbitrary specified phase 2 pulse widths between about one and three milliseconds to hyperpolarize the myocardium after the phase 1 shock has been delivered.

In another aspect of the invention, a method uses class A to Z or any other class of amplifier circuit topology to process arbitrary waveforms that deliver increasing energy with increasing time for a positive phase 1 and negative energy for phase 2 time periods that can range from about 500 ns to about 100 ms pulsed, chopped or continuous waveforms using any voltage for phase 1 and phase 2 from about 0 V to about +/−2200 VDC.

In another aspect of a method of the invention, a two-step electrical stimulus external pacing delivery system uses ascending or any arbitrary waveforms that are delivered by a servo amplifier array to pace and/or assist in restarting an asystole heart.

In another aspect of the invention, an apparatus or system for treating a cardiac condition in a human or animal patient comprises at least two electrode patches or paddles for contacting an area of skin of the patient, wherein the at least two electrode patches or paddles are capable of applying voltage and current in a rotational manner to pre-stimulate that area using a servo amplifier array and are capable of then delivering a high voltage shock through the patient's heart to effect defibrillation or cardioversion.

In another aspect of an apparatus or system of the invention, the at least two electrode patches or paddles are capable of delivering transcutaneous external pacing through the heart to assist in restarting an asytole heart.

In another aspect of an apparatus or system of the invention, an amplifier-based external defibrillation cardioversion system is used.

In another aspect of an apparatus or system of the invention, the cardioversion apparatus or system uses a two-step electrical stimulation comprising lower voltage biphasic arbitrary and ascending ramp high-voltage shocks that employ increasing energy with increasing time waveforms which are used to reduce peak voltages, reduce cardioversion and defibrillation energy, capture those patients who don't easily cardiovert or defibrillate, reduce perception of pain and reduce or eliminate burning of skin beneath external electrodes.

In another aspect of an apparatus or system of the invention, the apparatus or system uses differentially driven amplifier circuit topologies whereby biphasic arbitrary shock waveforms deliver increasing and or level energy with increasing time as represented by phase 1 ascending ramp, ascending exponential, ascending chopped, ascending stepped, ascending curved, square, rectilinear or level and or any combination of geometric shaped ascending or level waveforms which are delivered by any selection of three modes of software controlled defibrillation and or cardioversion shock waveforms which are (1) constant current, (2) constant voltage, or (3) constant energy for the purpose of controlling delivered defibrillation and or cardioversion electrical shocks to convert cardiac arrhythmias.

In another aspect of an apparatus or system of the invention, arrhythmias are treated.

In another aspect of the invention, an apparatus or system comprises an electrical servo amplifier array stimulator to deliver pre-stimulus low voltage pulses to cause skeletal muscle rotation and contraction, comprising the absolute refractory period of muscle contraction and lowering chest impedance.

In another aspect of an apparatus or system of the invention, the electrical servo amplifier servo array is capable of delivering in a second step a high voltage ascending waveform or any other biphasic arbitrary waveform shock, whether across the chest or between the front and back of a human chest, for conversion of AF, AT, VT or VF delivering a high-voltage shock ascending or level waveform, which will reduce perceived pain by lowering peak voltages and chest impedance, and also greatly reduce or eliminating the traditional first, second- and sometimes third-degree burns on the patient's skin under external electrodes since arbitrary ramp waveforms and a slower rate of change for the delivered energy are achieved.

In another aspect of the invention, the apparatus or system is capable, if a first cardioversion or defibrillation shock fails, of delivering another shock comprised of different biphasic wave forms to enhance and capture outlier patients that are difficult to cardiovert or defibrillate thereby increasing the overall rescue rate for patients that require cardioversion and or defibrillation.

In another aspect of the invention, an apparatus or system comprises class A to Z or any other class of amplifier circuit topology to process arbitrary waveforms that deliver increasing energy with increasing time for a positive phase 1 and negative energy for phase 2 time periods that can range from about 500 ns to about 100 ms pulsed, chopped or continuous waveforms using any voltage for phase 1 and phase 2 from about 0 V to about +/−2200 VDC.

In another aspect of an apparatus or system of the invention, a two-step electrical stimulus external pacing delivery system uses ascending or arbitrary waveforms that are delivered by a servo amplifier array to pace and/or assist in restarting an asystole heart.

In another aspect of the invention, in an improved system for defibrillation or cardioversion wherein shock waveforms are applied externally through a patient's heart, the improvement wherein all external defibrillation and/or cardioversion waveforms, pre-stimulus waveforms, and external pacing waveforms and capabilities employ ascending, level or any arbitrary geometry waveforms that are delivered using amplifier circuit topologies for successful cardioversion, defibrillation and or external pacing therapies.

In another aspect of the invention, in an improved system for defibrillation or cardioversion wherein shock waveforms are applied externally through a patient's heart, the improvement wherein the ideal output waveform is constructed from discrete points in time or equations stored in the uC which at each discrete time point, on the order of microseconds, the uC outputs a new waveform value thru a Digital to Analog converter (DAC) to the amplifiers and at each discrete time point, the current through the load is digitally converted using an Analog to Digital converter (ADC) using a digitized current that is averaged over multiple time samples to create a rolling average and whereby this rolling current average is used by the uC to calculate power and energy in real time for each discrete time point of the ideal output waveform in which the uC then increases or decreases the ideal output waveform to maintain the desired constant current or to achieve the desired total energy at the completion of the waveform, wherein current sense resistors provide electronic feedback to an uP for controlling the delivered servo amplifier voltages and currents.

The invention comprises a product possessing the features, properties, and the relation of components which will be exemplified in the product hereinafter described and the scope of the invention will be indicated in the claims.

BRIEF DESCRIPTION OF THE DRAWINGS

For a fuller understanding of the invention, reference is made to the following description taken in connection with the accompanying drawings, in which.

DETAILED DESCRIPTION OF THE DRAWINGS

Figure 1:
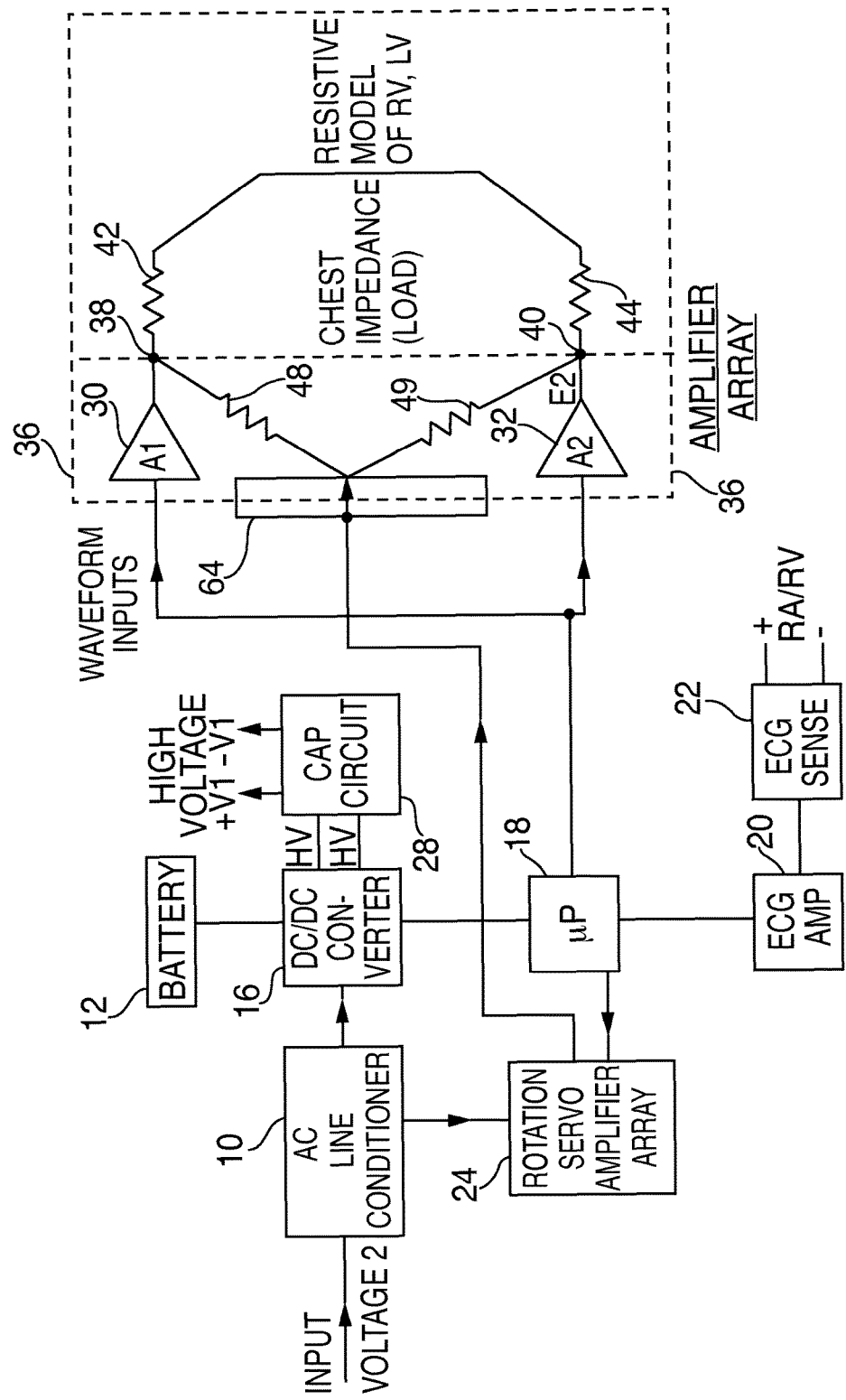
FIG. 1 represents a circuit diagram of one embodiment of the invention comprising an amplifier-based external ventricular cardioverter/defibrillation device and its major components and circuit architecture.

FIG. 1 illustrates one embodiment of a defibrillation system useful according to the invention. Input AC voltage 2 is processed via a line conditioner 10. A battery 12 provides power to a pulse width modulated (PWM) and regulated DC/DC converter 16, which in turn distributes a control voltage to a microprocessor 18, an ECG Amp 20, and an ECG Sense Analyzer 22 as well as a rotational servo amplifier array 24. DC/DC converter 16 also distributes high voltage to a capacitor circuit 28 and two amplifiers 30 and 32, within a patient's chest area 36. Electrodes 38 and 40 with their respective wires are external electrodes that are placed on the patient's chest as depicted in FIGS. 4 and 5.

According to the invention, the apparatus comprises an external defibrillator. According to another embodiment of the invention, the apparatus can treat VT of any mechanism, including but not limited to, automatic, triggered, or reentrant or VF, whether occurring in the structurally normal heart, hypertrophic heart, or myopathic heart (independent of origin of underlying structural heart disease). According to another embodiment of the invention, an apparatus for treating ventricular fibrillation or ventricular tachycardia comprises means for delivering a biphasic ascending exponential, ascending ramp, or any ascending waveform. Also illustrated are heart muscle resistances depicted by 42 and 44. These resistances represent the effective cardioversion/defibrillation load in which the voltage and current from the amplifiers deliver cardioversion/defibrillation shocks between two amplifiers simultaneously, as depicted by rotation and pre-stimulation circuits 64. Current sense resistors 48 and 49 provide electronic feedback to the uP 18 for controlling the delivered servo amplifier voltages and currents.

Figure 2:
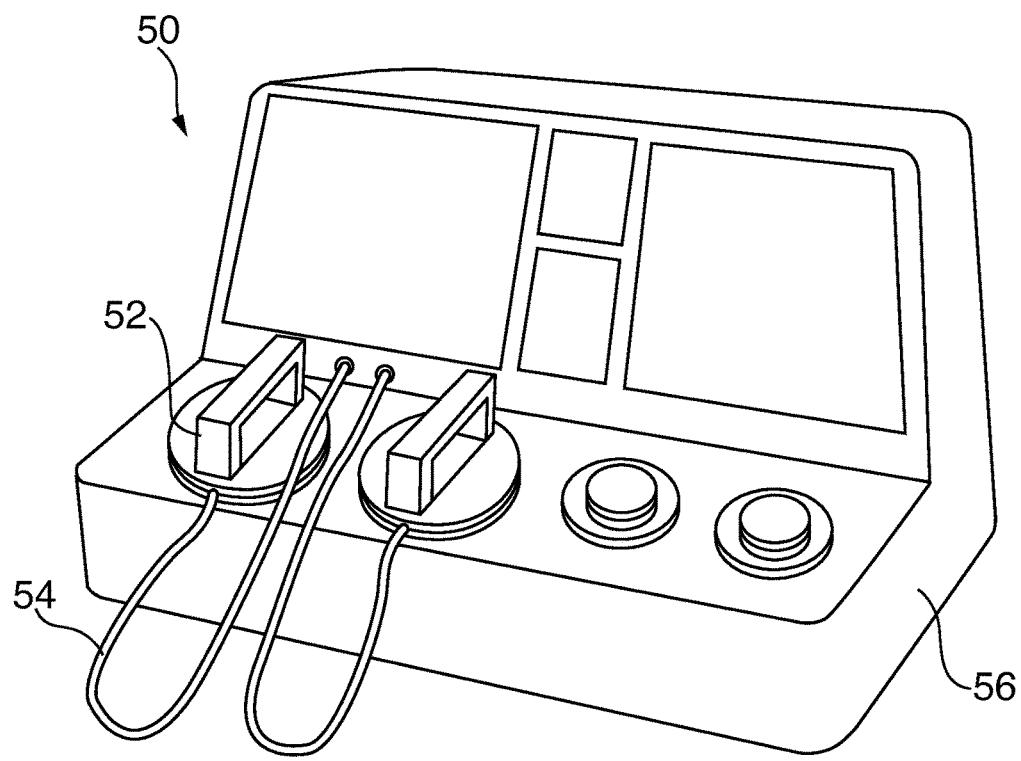
FIG. 2 represents a perspective view of an amplifier-based external ventricular cardioverter/defibrillation hospital grade device and the associated electrode paddles and or patches.

In FIG. 2, a typical hospital grade defibrillator system 50 comprises electrode paddles 52 connected by cables 54 to a console 56.

Figure 3:
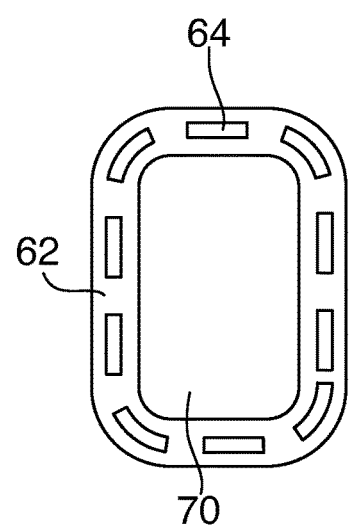
FIG. 3 represents a view of the electrode electrical surface that is in contact with a patient's chest and depicts the large high voltage conductive shocking electrode which also serves as the transcutaneous pacing electrodes as well as the rotational muscle contraction circuits for the purpose of delivering the pre-stimulus energy.

FIG. 3 shows the bottom or flat surface 62 of an electrode paddle or patch where printed circuits 64 are activated and powered by a microcontroller such as in console 56. Preferably the circuits are activated in a sequential, timed, pulsed manner to cause a rotational effect on the surface of the patient's skin. After application of a pulsed rotational energy from the servo amplifier array 24 for from about 1 to 4 seconds at a pulsed voltage of from about 10 V to about 80 V, a center portion 70 of the paddle or patch receives a high voltage shock for defibrillation or cardioversion of from about 800 to about 2200 V for from about 4 to about 100 ms. Center portion 70 also provides for the external transcutaneous pacing mode using ascending or arbitrary, constant current waveforms.

The external rotational muscle contraction pre-stimulation function and the transcutaneous pacing circuits use the same electronic circuits to deliver the voltage and currents to the chest muscle areas as shown in the drawings, including FIG. 3. The voltage ranges for both functions are the same and are commanded by different software commands when the device is in the desired and selected mode.

The ten, for example, conductive circuit pads 64 that surround the main high voltage electrode portion 70 depicted in the FIG. 3 are each electrically driven by a servo amplifier array which consists of ten individual servo amplifiers that are capable of low frequency pulses that can deliver electrical stimulus and pacing pulses from direct current (DC) to about 100 Hz differentially. This means that any of the ten amplifiers can be driven through the chest muscle to any other amplifier within one electrode patch or paddle in a rotational fashion to deliver the pre-stimulus contractions, and when the pacing selection is made, any or all of the amplifiers within each patch or paddle electrode may be driven across the chest between patches or paddles individually or in unison as to maximize the ability to capture the heart conduction system for the purpose of external pacing. The software commands shall have several selectable modes of rotational stimulus as to achieve the optimum contraction for the pre-stimulus function and software commands for the external pacing shall be configured to deliver optimum delivery for the best possible cardiac capture to ensure an exceptionally reliable conduction current from about 30 ma to 50 ma through the chest and heart muscle for the purpose of external cardiac pacing. A voltage range from about 10 V to about 80 V is provided via the servo amplifier array to accommodate the wide range of chest impedance to achieve a successful external pacing therapy. The electronics shall contain a current sensing feature whereby information from the chest impedance and resulting current is then used as feedback to the microcontroller—so the software commands will automatically adjust the delivered voltage and current for the purpose of external pacing between patches or paddle electrodes or optimized pre-stimulation of the chest muscle beneath the electrode patches or paddles.

Figure 4A:
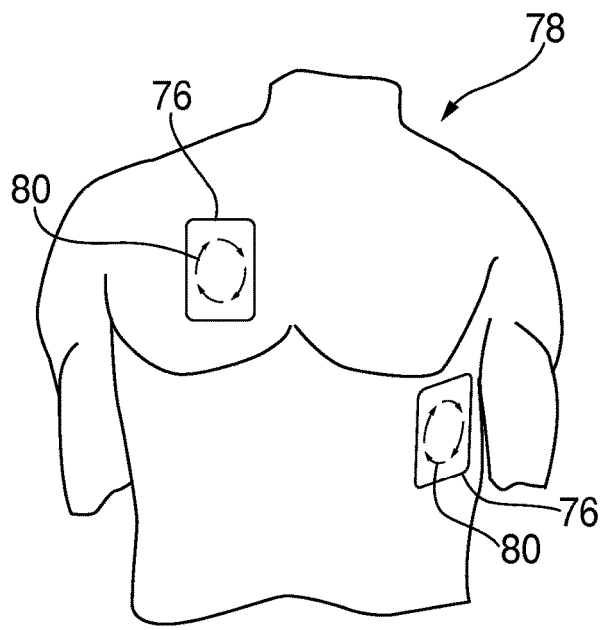
FIG. 4A and FIG. 4B are schematic representations of application of pre-stimulation and actual high voltage shock to a patient or an transcutanious pacing therapy.
Figure 5:
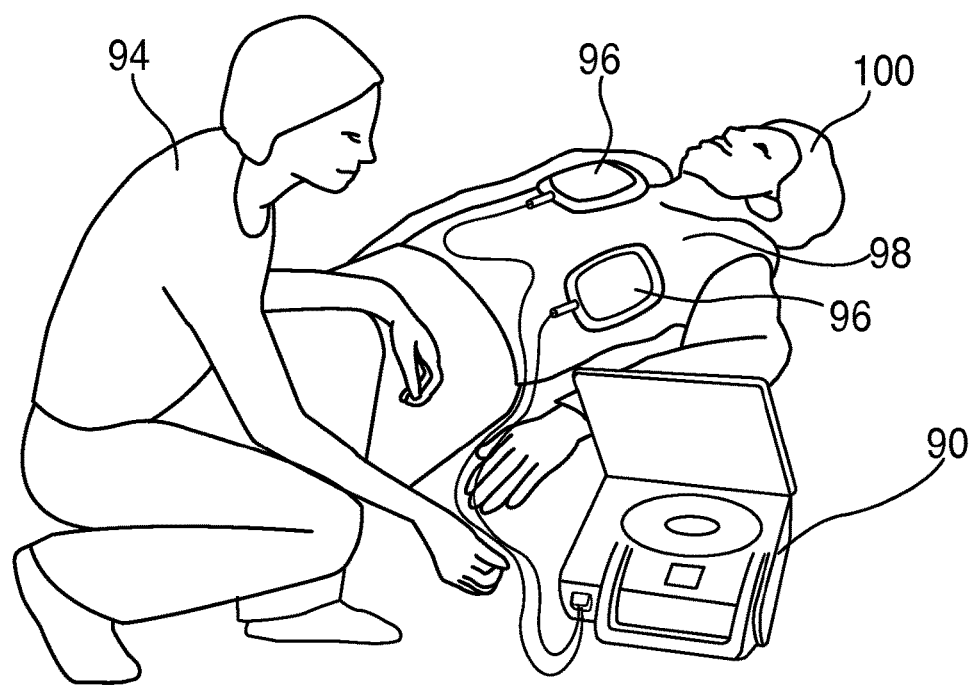
FIG. 5 is a representation of a system overview of an amplifier-based external ventricular cardioverter/defibrillation electrode placement and the associated two step cardioversion/defibrillation process in an AED setting being used to cardiovert/defibrillate a patient.

In FIG. 4A, two electrode paddles or patches 76 are spaced apart on the surface of the skin of a patient 78. Curved arrows 80 represent the intended rotational path of electrical current administered during the pre-stimulation step. The rotational current 80 delivered from the servo amplifier array 24 is intended to stimulate muscle mass to its absolute refractory period prior to application of the primary defibrillation, cardioversion shock.

Figure 4B:
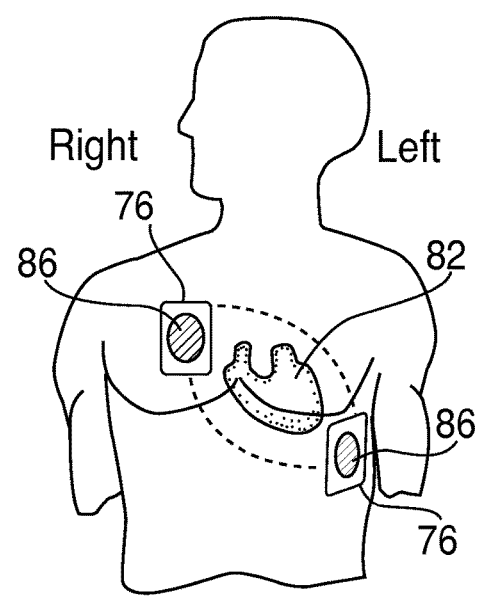

As shown in FIG. 4B, electrode paddles or patches 76 are positioned on either side of the patient's heart 82. The darkened area 86 in each electrode paddle or patch 76 represents application of the primary defibrillation shock. Together, FIGS. 4A and 4B represent a system overview of an amplifier-based external ventricular cardioverter/defibrillation electrode placement and the associated two step cardioversion/defibrillation process.

In FIG. 5, treatment with an AED is shown. The AED device 90 is an external defibrillator that checks heart rhythm and can send electric shocks to restore normal rhythm. Device 90 has written instructions and gives voice instructions to an operator 94. Operator 94 will position electrode patches or paddles 96 on the chest area 98 of patient 100, so that they adhere and conduct electricity very well to chest area 98. Consistent with an embodiment of the invention herein, electrode patches or paddles 96 will be configured with circuits to apply rotational current (not shown) prior to application of a defibrillation shock.

Figure 6A:
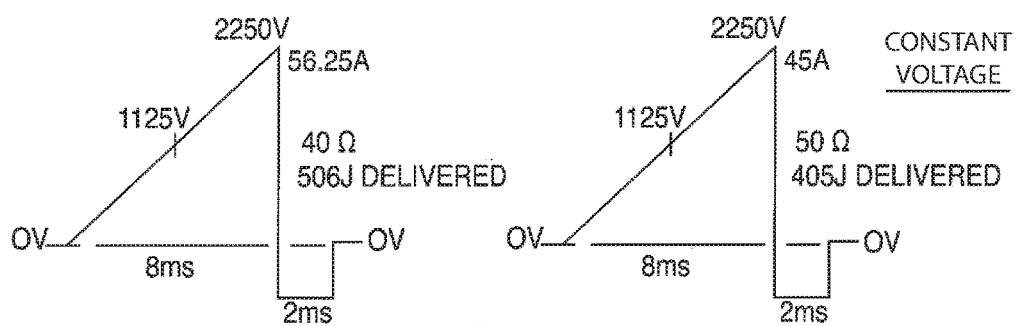
FIGS. 6A to 6C represent amplifier-generated ascending ramp shock waveform examples delivered with constant voltage, constant current, and constant energy modes of operation, respectively. Impedance, voltage and currents delivered in examples are shown.
Figure 6B:
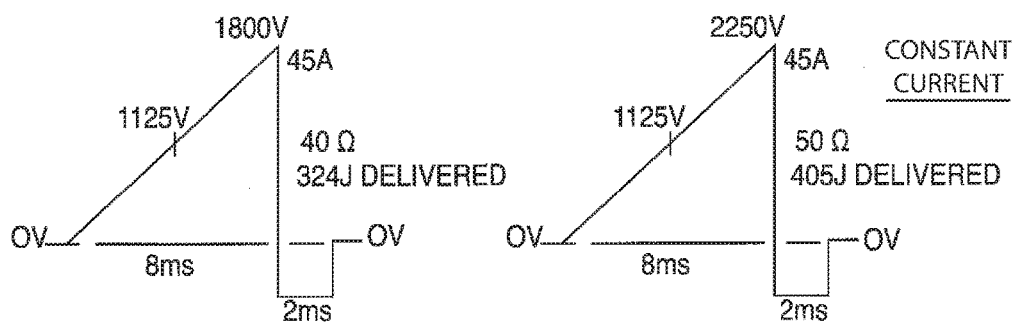
Figure 6C:
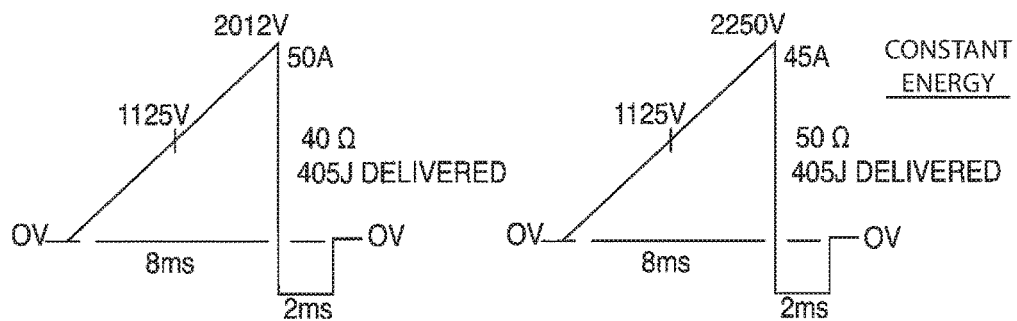

FIGS. 6A to 6C depict typical amplifier-generated ascending ramp shock waveform examples which are represented in constant voltage (FIG. 6A), constant current (FIG. 6B), and constant energy (FIG. 6C) modes of operation. Impedance, voltage and currents delivered in examples are shown. In each figure, the left waveform is based upon a chest impedance of 40 ohms, and the right waveform is based upon a chest impedance of 50 ohms.

For FIG. 6A, constant voltage, in the 40 ohm example, the voltage remains the same as in the 50 ohm example. However in the 40 ohm example, current increases and the delivered energy increases.

For FIG. 6B, constant current, in the 40 ohm example, the current remains the same as in the 50 ohm example. However in the 40 ohm example, voltage decreases and the delivered energy decreases.

For FIG. 6C, constant energy, in the 40 ohm example, the energy remains the same as in the 50 ohm example. However in the 40 ohm example, voltage decreases and the delivered current increases.

To those skilled in the art and science of cardioversion and/or defibrillation, a "constant current" shock is preferred since in any electrical system it is the "current" or force that does the "work". Voltage levels are just potentials or stored voltage levels and energy is the product of voltage x current which equals power in watts and V×I=W×Time=Watt/Seconds or Joules of energy.

It will thus be seen that the objects set forth above, among those made apparent from the preceding description are efficiently attained and, since certain changes may be made in the devices and methods set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention, which, as a matter of language, may be said to fall there between.

We claim:

1. A method for treating a cardiac condition in a patient, comprising:
   contacting an area of outer skin of the patient with at least two external multi-electrode patches or paddles that apply current in a rotational manner to pre-stimulate that area;
   in a first step applying a low-voltage electrical current beneath the at least two external multi-electrode patches or paddles in a rotational manner to pre-stimulate that area, causing chest muscle beneath the multi-electrode patches or paddles to contract to an absolute refractory period and lowering chest muscle impedance, thereby providing a low impedance chest pathway using less energy compared to standard defibrillation devices; and
   in a second step applying a high voltage arbitrary waveform shock from the multi-electrode patches or paddles through the patient's chest and heart to cause defibrillation, cardioversion, or defibrillation and cardioversion.

2. The method of claim 1, wherein an amplifier-based external defibrillation cardioversion system is used.

3. The method of claim 2, wherein the cardioversion system uses a two-step electrical stimulation comprising biphasic arbitrary and ascending ramp high-voltage shocks that employ increasing energy with increasing time waveforms which are used to reduce peak voltages, reduce cardioversion and defibrillation energy, capture those patients who don't easily cardiovert or defibrillate, reduce perception of pain, and reduce or eliminate burning of skin beneath external electrodes.

4. The method of claim 2, wherein the system uses differentially driven amplifier circuit topologies whereby biphasic arbitrary shock waveforms deliver increasing and/or level energy with increasing time as represented by phase 1 ascending ramp, ascending exponential, ascending chopped, ascending stepped, ascending curved, square, rectilinear or level and or any combination of geometrically shaped ascending or level waveforms which are delivered by any selection of three modes of software-controlled defibrillation and/or cardioversion shock waveforms which are (1) constant current, (2) constant voltage, or (3) constant energy for the purpose of controlling delivered defibrillation and or cardioversion electrical shocks to convert cardiac arrhythmias.

5. The method of claim 1, wherein arrhythmias are treated.

6. The method of claim 1, whereby qualified medical professionals first apply electrode patches or paddles and then an electrical servo amplifier array stimulator delivers pre-stimulus low voltage pulses to cause skeletal muscle rotation and contraction, comprising the absolute refractory period of muscle contraction and lowering chest impedance.

7. The method of claim 6, wherein in a second step a high voltage ascending waveform or any other biphasic arbitrary waveform shock is delivered, whether across the patient's chest or between the front and back of the patient's chest, for conversion of AF, AT, VT, or VF delivering a high-voltage shock ascending or level waveform, which will reduce perceived pain by lowering peak voltages and chest muscle impedance, and also greatly reduce or eliminate the traditional first-, second- and sometimes third-degree burns on the patient's skin under external electrodes since arbitrary ramp waveforms and a slower rate of change for the delivered energy are achieved.

8. The method of claim 1, wherein, if a first cardioversion or defibrillation shock fails, another shock comprised of different biphasic waveforms will be delivered to capture outlier patients who are difficult to cardiovert and/or defibrillate, thereby increasing the overall rescue rate for patients who require cardioversion and/or defibrillation.

9. The method of claim 1, wherein a phase 2 shock voltage is "hard-switched" negative with respect to a zero crossing point to any specified negative voltage potential, and narrow arbitrary specified phase 2 pulse widths between about one and three milliseconds are used to hyperpolarize the myocardium after a phase 1 shock has been delivered.

10. The method of claim 1 which uses class A to Z or any other class of amplifier circuit topology to process arbitrary waveforms that deliver increasing energy with increasing time for a positive phase 1 and negative energy for phase 2 time periods that can range from about 500 ns to about 100 ms pulsed, chopped, or continuous waveforms using any voltage for phase 1 and phase 2 from about 0 V to about +/−2200 VDC.

11. The method of claim 1, wherein a two-step electrical stimulus external pacing delivery system uses ascending or any arbitrary waveforms that are delivered by a servo amplifier array to pace and/or assist in restarting an asystole heart.

12. An apparatus for external treatment of a cardiac condition in a patient, comprising:
  at least two multi-external electrode patches or paddles for contacting an area of the outer surface of skin of the patient;
  a pre-stimulus servo amplifier array; and
  an external waveform energy software control system which comprises:
    an electronic system containing a microcontroller programmed with software; and
    external differentially driven amplifier circuits having an input and an output,
  wherein the microcontroller is operatively connected to the input of the differentially driven amplifier circuits, the microcontroller is configured to respond to software commands to generate signals to the input of the differentially driven amplifier circuits, and the output of the differentially driven amplifier circuits externally delivers constant current, constant energy, or constant voltage ascending arbitrary ramp waveforms, biphasic truncated exponential (BTE) waveforms, or ascending arbitrary and BTE descending waveforms, transcutaneous pacing, low voltage therapies, defibrillation, or cardioversion electrical shocks through the at least two external multi-electrode patches or paddles, through the patient's skin, to the patient's heart, and
  wherein in a first step the pre-stimulus servo amplifier array delivers a low-voltage electrical current beneath the at least two external multi-electrode patches or paddles in a rotational manner to pre-stimulate that area, causing chest muscle beneath the multi-electrode patches or paddles to contract to an absolute refractory period and lowering chest muscle impedance, thereby providing a low impedance chest pathway using less energy compared to standard defibrillation devices, and
  wherein in a second step the differentially driven amplifier circuits deliver a high voltage arbitrary waveform shock from the multi-electrode patches or paddles through the patient's chest and heart to cause defibrillation, cardioversion, or defibrillation and cardioversion.

13. The apparatus of claim 12, wherein the at least two external multi-electrode patches or paddles are capable of delivering transcutaneous external arbitrary pacing pulses and/or low or high voltage therapies through the patient's chest and heart to restart an asystole heart.

14. The apparatus of claim 12, wherein the system uses differentially driven amplifier circuit topologies whereby external biphasic arbitrary shock waveforms deliver increasing and/or level energy with increasing time as represented by phase 1 or phase 2 ascending ramp, ascending exponential, ascending chopped, ascending stepped, ascending curved, square, rectilinear, BTE, or level and/or any combination of geometrically shaped ascending or level waveforms which are delivered by any selection of three modes of software-controlled defibrillation and/or cardioversion shock waveforms which are (1) constant current, (2) constant energy, or (3) constant voltage for the purpose of controlling delivered defibrillation and/or cardioversion electrical shocks to convert cardiac arrhythmias.

15. The apparatus of claim 12, wherein cardiac arrhythmias are treated.

16. The apparatus of claim 12, wherein the servo amplifier array delivers pre-stimulus low voltage pulses beneath each multi-electrode area to cause skeletal muscle rotation and contraction, comprising the absolute refractory period of muscle contraction and lowering chest muscle impedance.

17. The apparatus of claim 16, wherein the differentially driven amplifier circuits deliver a high voltage ascending arbitrary waveform, BTE, or any other biphasic arbitrary waveform shock, whether across the patient's chest or between the front and back of the patient's chest, for conversion of AF, AT, VT, or VF, which reduces perceived pain by lowering peak voltages and chest impedance and also greatly reduces or eliminates burns on the patient's skin under external multi-electrodes.

18. The apparatus of claim 12, wherein, if a first cardioversion or defibrillation shock fails, the system software will analyze why the shock failed and cause the apparatus to deliver another external shock comprised of different biphasic waveform geometries to increase capture of outlier patients that are difficult to cardiovert and/or defibrillate, thereby increasing the overall rescue rate for patients who require cardioversion and/or defibrillation.

19. The apparatus of claim 12 which comprises external differentially driven amplifier circuits to process arbitrary biphasic waveforms that deliver increasing energy with increasing time for a positive phase 1 and negative energy for phase 2 time periods that can range from about 500 ns to about 100 ms pulsed, chopped, or continuous waveforms using any voltage for phase 1 and phase 2 from about 0 V to about +/−2200 VDC.

20. The apparatus of claim 12, wherein ascending, level, or BTE arbitrary waveforms are delivered by the differentially driven amplifier circuits to pace and/or assist in restarting an asystole heart.

21. The apparatus of claim 12, wherein the external waveform energy control system also comprises a digital-to-analog converter (DAC) and wherein the microcontroller is operatively connected to the DAC, the DAC is operatively connected to the input of the differentially driven amplifier circuits, the microcontroller is configured to respond to software commands to generate signals to the DAC, the DAC provides signals to the input of the differentially driven amplifier circuits, and the output of the differentially driven amplifier circuits delivers constant current, constant voltage, or constant energy employing ascending, level, or BTE waveform shocks for cardioversion and/or defibrillation, or ascending, level and BTE waveforms for pacing through the patient's heart.

22. The apparatus of claim 21, wherein the waveform energy control system is capable of applying shock waveforms externally through a patient's heart and chest and an output waveform is constructed from discrete points in time or equations stored in the microcontroller which at each discrete time point, on the order of microseconds, the microcontroller outputs a new waveform value through the DAC to the amplifiers and at each discrete time point, the current through the patient's chest and heart is sampled and converted using an analog-to-digital converter (ADC) wherein a digitized current signal is generated from the sense resistors providing electronic feedback to the microcontroller and is sampled at multiple intervals, creating a rolling current average used by the microcontroller and software to calculate power, energy, and voltage in real time for each discrete time point of the output waveform in which the microcontroller then increases or decreases the output waveform amplitude commands to maintain the desired constant current, constant energy, or constant voltage.

23. The apparatus of claim 12 which is an AED, EMS/EMT, or hospital grade cardioverter-defibrillator system.

24. A system for external treatment of a cardiac condition in a patient, comprising:
- at least two external multi-electrode patches or paddles for contacting an area of the outer surface of skin of the patient;
- a pre-stimulus servo amplifier array; and
- an external waveform energy software control system which comprises a microcontroller; and
- differentially driven amplifier circuits having an input and an output,
- wherein the microcontroller is operatively connected to the input of the differentially driven amplifier circuits, the microcontroller is configured to respond to software commands to generate signals to the input of the differentially driven amplifier circuits, and the output of the differentially driven amplifier circuits externally delivers defibrillation or cardioversion electrical shocks through the at least two external multi-electrode patches or paddles, through the patient's chest, to the patient's heart, and
- wherein in a first step the pre-stimulus servo amplifier array delivers a low-voltage electrical current beneath the at least two external multi-electrode patches or paddles in a rotational manner to pre-stimulate that area, causing chest muscle beneath the multi-electrode patches or paddles to contract to an absolute refractory period and lowering chest muscle impedance, thereby providing a low impedance chest pathway using less energy compared to standard defibrillation devices, and
- wherein in a second step the differentially driven amplifier circuits deliver a high voltage arbitrary waveform shock from the multi-electrode paddles or patches through the patient's chest and heart to cause defibrillation, cardioversion, or defibrillation and cardioversion.

* * * * *